(12) United States Patent
Amirav et al.

(10) Patent No.: US 9,034,077 B2
(45) Date of Patent: May 19, 2015

(54) FAST GAS CHROMATOGRAPH METHOD AND DEVICE FOR ANALYZING A SAMPLE

(71) Applicants: Aviv Amirav, Hod Hasharon (IL); Alexander B. Fialkov, Tel Aviv (IL)

(72) Inventors: Aviv Amirav, Hod Hasharon (IL); Alexander B. Fialkov, Tel Aviv (IL)

(73) Assignee: Aviv Amirav, Hod Hasharon (IL)

( * ) Notice: Subject to any disclaimer, the term of this patent is extended or adjusted under 35 U.S.C. 154(b) by 44 days.

(21) Appl. No.: 14/062,769

(22) Filed: Oct. 24, 2013

(65) Prior Publication Data
US 2014/0047900 A1    Feb. 20, 2014

Related U.S. Application Data

(63) Continuation-in-part of application No. 12/899,288, filed on Oct. 6, 2010, now Pat. No. 8,591,630.

(51) Int. Cl.
| | |
|---|---|
| G01N 30/60 | (2006.01) |
| G01N 30/30 | (2006.01) |
| G01N 30/46 | (2006.01) |
| G01N 30/72 | (2006.01) |

(52) U.S. Cl.
CPC ........ G01N 30/60 (2013.01); *G01N 2030/3084* (2013.01); G01N 30/30 (2013.01); *G01N 30/463* (2013.01); *G01N 30/7206* (2013.01); *G01N 2030/3061* (2013.01); *G01N 2030/3069* (2013.01); *G01N 2030/3076* (2013.01)

(58) Field of Classification Search
CPC ....... G01N 30/16; G01N 30/30; G01N 30/60; G01N 30/461; G01N 30/463; G01N 30/468; G01N 2030/3053; G01N 2030/3061; G01N 2030/3069; G01N 2030/3076; G01N 2030/3084
See application file for complete search history.

(56) References Cited

U.S. PATENT DOCUMENTS 5,808,178 A * 9/1998 Rounbehler et al. ......... 73/23.39

* cited by examiner

*Primary Examiner* — Robert Clemente
(74) *Attorney, Agent, or Firm* — Davis Wright Tremaine LLP (57) ABSTRACT

A fast gas chromatograph (GC) method and device for obtaining fast gas chromatography analysis, in which a capillary gas chromatography column is inserted into a resistively heated metal tube located mostly outside a heated oven, which serves as a heated transferline to a flexible column that enters a resistively heated metal tube from a gas chromatograph injector and exits into a gas chromatograph detector. The resistively heated metal tube of the fast GC device has an internal diameter that is over twice the external diameter of the GC column so as to enable the insertion of several capillary GC column loops. The process of column insertion into or removal from the heated tube is aided by touching it with an ultrasound vibrating device that remarkably reduces the friction during column insertion into the metal tube heater.

34 Claims, 2 Drawing Sheets

FAST GAS CHROMATOGRAPH METHOD AND DEVICE FOR ANALYZING A SAMPLE

CROSS-REFERENCE TO RELATED APPLICATIONS

The present invention is a continuation-in-part of U.S. patent application Ser. No. 12/899,288, filed on Oct. 6, 2010 and entitled FAST GAS CHROMATOGRAPH METHOD AND DEVICE FOR ANALYZING A SAMPLE.

FIELD OF THE INVENTION

Certain aspects of the invention relate to an improved fast gas chromatograph (GC) method and device for obtaining fast gas chromatography and/or fast gas chromatography mass spectrometry analysis.

BACKGROUND OF THE INVENTION

Gas chromatography is a central analytical technology having a large variety of applications in a broad range of fields, especially when used in association with mass spectrometry for improved sensitivity, selectivity and sample identification capability. However, while gas chromatography (GC) is a powerful analytical tool, GC analysis requires long analysis times, typically in the order of 30-60 min when operated with standard gas chromatography columns (typically 30 m) combined with standard GC ovens with their slow temperature programming rate and slow cooling down for being ready to next analysis.

In view of the long time associated with standard GC analysis, several fast GC systems have been developed that incorporate low thermal mass devices that provide fast temperature programmable heating and cooling rates for the GC separation columns.

Relevant and related to this application is US 2012-0085148, which discloses a low thermal mass fast GC, based on the transfer of a gas chromatography column through a gas chromatograph oven as a flexible non-rigid capillary into a resistively heated metal tube having opposing input and output ends. The input and output ends of the resistively heated metal tube are located near a hole in the gas chromatograph oven body so that a substantial portion of the column in the heated metal tube is located outside the gas chromatograph oven and so that the input and output ends project a short distance inside the gas chromatograph oven. The capillary column is connected in the gas chromatograph oven as a flexible capillary with both the gas chromatograph injector and detector. Both ends of the resistively heated metal tube are connected to a power supply that resistively heats the heated metal tube in a time programmed manner to facilitate fast temperature program of the capillary column.

An important feature of the fast gas chromatograph according to US 2012-0085148 is that the capillary column and the resistively heated metal tube are configured such that transferring the capillary column through the gas chromatograph oven into the resistively heated metal tube and introducing the capillary column from the heated metal tube into the gas chromatograph oven is reversible, without removal of the resistively heated metal tube. However, the fast gas chromatograph disclosed in this reference is still subject to a few limitations including the following:

1. Friction in column insertion. The process of column insertion into the heated metal tube is involved with friction that increases as the heated metal tube length is increased, particularly if the internal diameter of the heated metal tube is not much larger than the outer diameter of the GC capillary column as is desirable for minimizing the heated tube thermal mass. This friction is largely increased due to the curving and coiling of the heated metal tube to diameters such as 12-15 cm in order to have small fast GC house dimension. It can also emerge and increase from imperfect coiling. As a result of this friction and in order to enable safe in-field column replacement by the fast GC users, the heated metal tube length and with it the capillary column length is restricted to typically 2 m such that fast GC separation is impeded.
2. Possible capillary column breakage. The insertion of the fused silica gas chromatography capillary columns into the narrow resistively heated metal tube is a delicate process that could lead into the breakage of the fused silica capillary column inside the metal heating tube with difficulties to remove the broken capillary pieces. GC capillary columns are delicate as their brittle fused silica tube thickness is only about 40µ and although they are supported by Vespel plastic they are still delicate. Furthermore, the heated metal tube often includes some imperfections that can scratch the thin protective Vespel layer and lead this way to column breakage.
3. Fixed small heated metal tube and capillary column length. The resistively heated metal tube is heated and operated with a power supply. The heated tube temperature depends on the heating current (power per unit length) while its operational voltage linearly increases with the tube length and with it the total power requirements from the power supply as well as the power supply size, weight and cost, and similarly the size and cost of the related cooling fans. Furthermore, higher voltage is also not as safe. Thus, for practical electrical power saving reasons the length of the heated tube metal is restricted. The heated metal tube length restriction also emerges from the growing friction with its length and with it the danger to the column integrity during its insertion into the heating metal tube. Consequently the length of the fused silica capillary column is restricted and its separation capability is limited due to its limited length. Even if the power supply could provide any needed voltage, once the heated metal tube length is provides in a given length, the GC capillary column length is fixed and cannot be changed which reduces the fast GC flexibility in trade-off of separation and speed of analysis.

Thus, it is desirable to improve the fast GC according to US 2012-0085148 by reducing friction between the capillary column and its heated metal tube oven during the capillary column insertion or removal for its replacement. Reducing friction will reduce the chances of column breakage during its insertion. Furthermore, it is also important to enable freedom in the selection of capillary column length while complying with the length limitation of the heated metal tube. These challenges are addressed in novel and unexpected ways by the present invention.

BRIEF DESCRIPTION OF THE INVENTION

It is an object of the present invention to provide an improved method and system for fast gas chromatography analysis.

In accordance with one aspect of the invention, there is provided a method for fast gas chromatography analysis, said method comprising:

injecting a sample to be analyzed into a gas chromatograph injector that is flexibly coupled to a gas chromatography capillary column;

transferring said sample in said injector into said capillary column with a carrier gas flow;

transferring said capillary column through a heated oven as a flexible non-rigid capillary into a resistively heated metal tube having opposing input and output ends;

locating the input and output ends of said resistively heated metal tube near a hole in said heated oven body so that a substantial portion of said column in said heated metal tube is located outside said heated oven and so that said input and output ends project a short distance inside said heated oven;

introducing an end of said portion of said capillary column that is outside the heated oven from said heated metal tube into said heated oven as a flexible capillary, wherein the capillary column and the resistively heated metal tube are configured such that transferring the capillary column through the heated oven into the resistively heated metal tube and introducing the capillary column from the heated metal tube into the heated oven is reversible, without removal of the resistively heated metal tube;

connecting said flexible capillary with a transfer line that leads into a gas chromatograph detector;

connecting both ends of said resistively heated metal tube to a power supply; and resistively heating said heated metal tube in a time programmed manner to facilitate fast temperature program of said capillary column;

wherein:

the resistively heated metal tube has an internal diameter that is over twice the external diameter of the capillary gas chromatograph column.

BRIEF DESCRIPTION OF THE DRAWINGS

The invention will now be described in connection with certain preferred embodiments with reference to the following illustrative figures, so that it may be more fully understood. With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of the claims.

In the drawings.

DETAILED DESCRIPTION OF THE INVENTION

Figure 1:
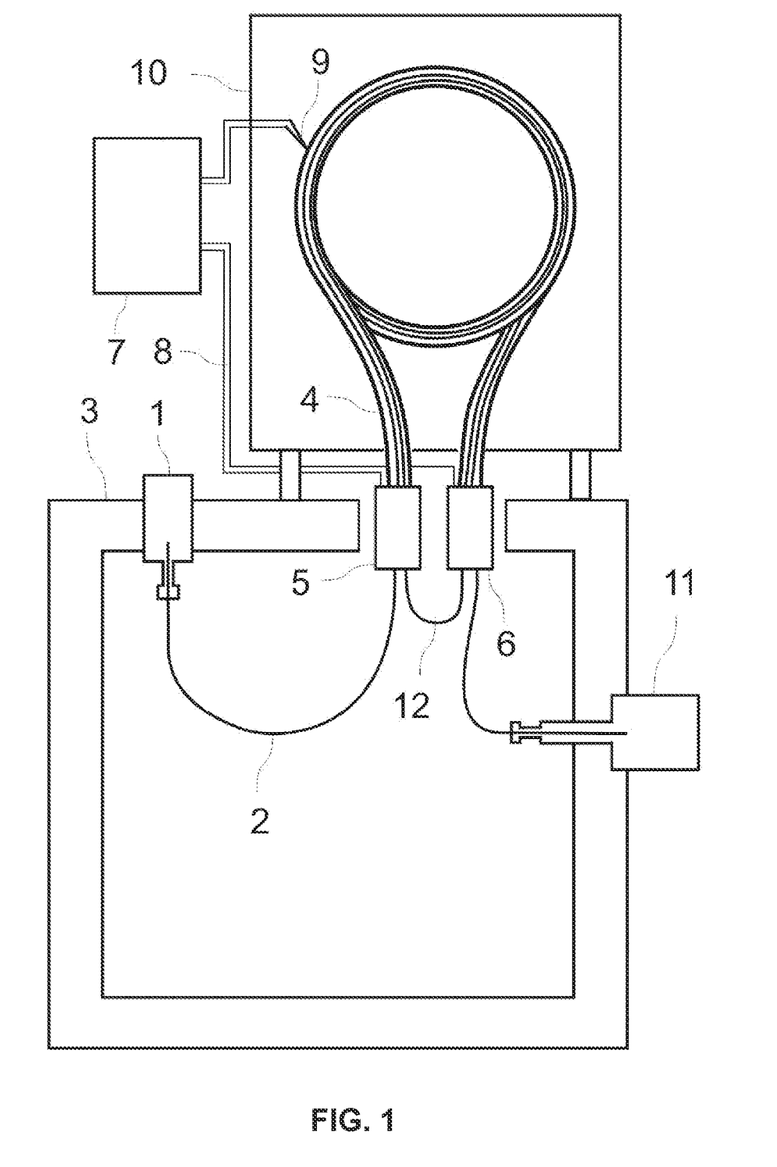
FIG. 1 is a schematic diagram illustrating the fast gas chromatograph device according to the present invention.

FIG. 1 shows schematically the novel fast gas chromatograph according to the present invention. A sample is injected as usual manually or with an autosampler into a GC injector (1) which is connected to a conventional capillary GC column (2). The capillary column is connected to the injector in a flexible non-rigid way as is normally done with standard GCs but in contrast to most fast GCs. The capillary column itself is typically made from flexible VESPEL™ coated fused silica tubing, coated on its inside with a thin sorption film. The column is immersed in a heated oven (3) which can be a small heated chamber oven that is designed for low space and power consumption or the air heated and cooled temperature programmable oven of a standard gas chromatograph that is converted to operate as a fast gas chromatograph. The heated oven in which the column is immersed must be heated to a temperature that corresponds to the temperatures of the injector and detector to eliminate cold spots. The capillary GC column is introduced into a metal tube (4) that can be resistively heated and which has an inlet (5) and an outlet (6), both of which are connected to a current programmed power supply (7) via electrical connections (8). The power supply (7) includes temperature sensor feedback and is capable of being current programmed to provide a temperature program (with time). The temperature can be measured with a thermocouple (9), or via the resistance of the metal tube which increases with its temperature in known manner. Otherwise, the current value can be used alone to represent the temperature via temperature calibration tables. The capillary column in its resistively heated metal tube is mostly located in an air-cooled enclosure (10) which is placed outside the heated oven or above a standard GC oven if a standard GC oven acts as the heated oven (3). Within the context of the invention and the appended claims, the term "standard" as applied to the GC oven refers to any commercially available GC oven i.e. not one having the enhancements according to the invention. The inlet (5) and the outlet (6) of the heated metal tube are located just at the edge of the heated oven (3) housing so that the portion of it that is not resistively heated is located inside the heated oven so that it will be heated to the heated oven temperature. The portion that is resistively heated is located just outside the heated oven to avoid or significantly reduce its double heating by both the heated oven and resistively heated tube, which can lead into an over-heated column section (hot spot) as well as to avoid unheated sections of the GC column (cold spot) between the resistively heated tube and heated oven. The inlet and outlet union of the heated metal tube provide smooth temperature gradient between portions of the capillary column located inside the GC oven and its portion located inside the heated metal tube. Both hot spot and cold spot, permanent or temporary (during temperature program) appearance are unacceptable. Hot spot causes the reduction of the column lifetime, induces local damage to the column separation film and protective VESPEL™ external film, increases column bleed, degrades thermally labile analytes and can lead to column breakage, while cold spot affects chromatographic peak shape and induces peak tailing and delays or precludes the elution of low volatility analytes. Therefore, the proper location of the inlet (5) and outlet (6) unions and their design is aimed at minimizing both hot and cold spots. The capillary column output is flexibly connected to the separately heated detector transfer line (11). According to the present invention, the detector can be any standard GC detector such as a flame ionization detector (FID), flame photometric detector (FPD), nitrogen phosphorus detector (NPD), electron capture detector (ECD) or thermal conductivity detector (TCD), or a mass spectrometer (MS).

Unique to the present invention is that the resistively heated metal tube (4) has an internal diameter that is over twice the external diameter of the capillary GC column so that several loops of capillary columns can be inserted into the heated metal tube (4). As an example, one of the standard fused silica capillary column has an internal diameter of 250 μ and external diameter of 360μ while the heated metal tube that we used has an internal diameter of 1.27 mm (0.050") and external diameter of 1.56 mm (1/16"). Accordingly, the capillary GC column is inserted into the heated metal tube inlet (5), exit its outlet (6) and then folded back with about 15 cm loop (12) as shown in FIG. 1 and reinserted into inlet (5) for having a second column loop while exiting again from outlet (6). With the heated metal tube dimensions as above this process can be repeated, for example, four times so that the column length inside the heated metal tube (that serves for fast GC separation) can be, for example, selected to be the heated metal tube length itself or twice that length or three times that length or four times that length. As a result, the fast GC according to the present invention allows its users to trade analysis time with separation efficiency as optimal for their needs without changing the heated metal tube and or its control power supply.

Another benefit that emerges from the use of a heated metal tube with an internal diameter that enables the insertion of several loops of a capillary GC column is that it can also accommodate two different capillary GC columns. Accordingly, the fast GC may have two injectors and either one or two detectors and two short columns that are connected to two different injectors and that are inserted into the heated metal tube. As a result, the user can analyze different samples with two different column types while having only a one low thermal mass heated metal tube as the GC separation oven and column switching can be automated via a method change.

Figure 2:
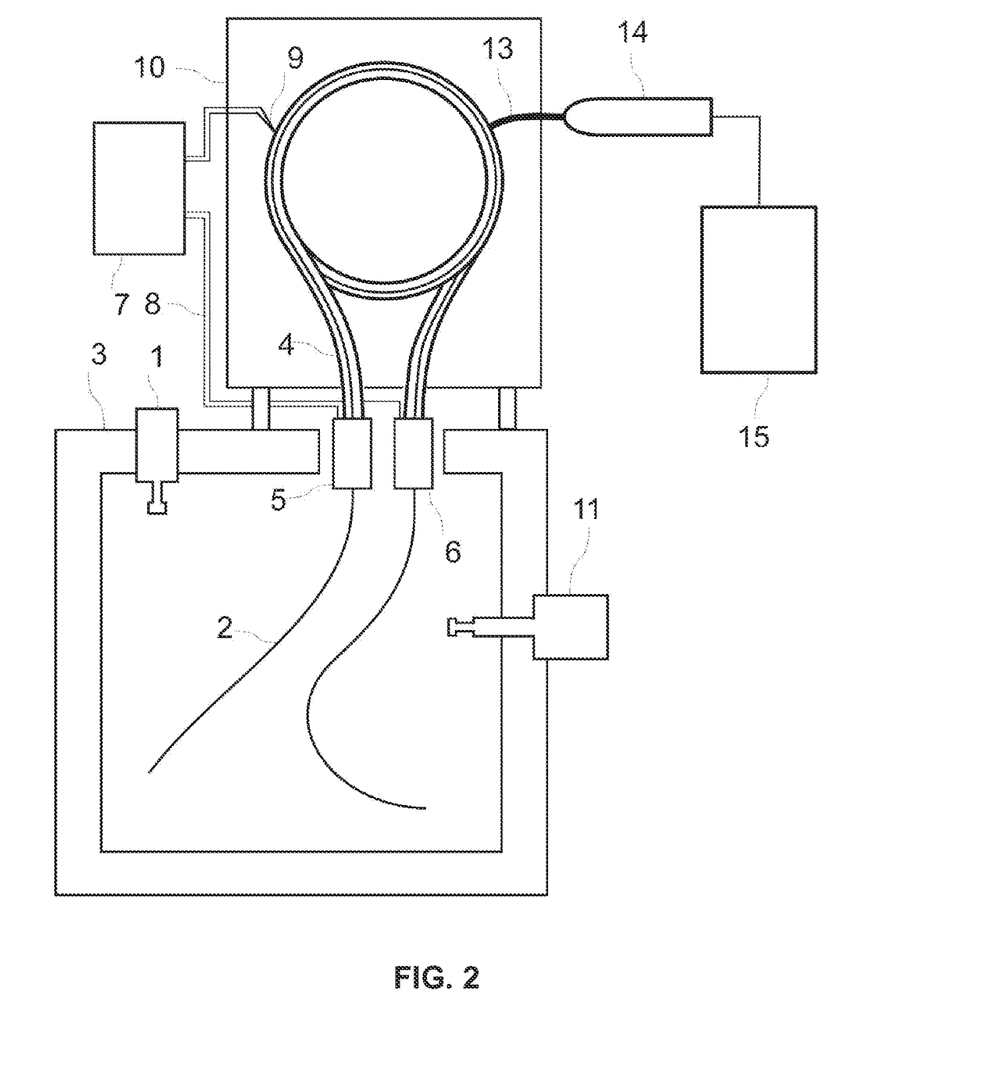
FIG. 2 is a schematic diagram illustrating an additional embodiment of the fast gas chromatograph device according to the invention.

FIG. 2 shows schematically the novel fast gas chromatograph according to another important improvement that is provided by the present invention. Accordingly and as shared with FIG. 1 above, the sample can be injected as usual manually or with an autosampler into a GC injector (1) which can be connected to a conventional capillary column (2) (the connection is not shown in FIG. 2). The capillary column itself is typically made from flexible VESPEL™ coated fused silica tubing, coated on its inside with a thin sorption film. The column is immersed in a heated oven (3) which can be a small heated chamber oven that is designed for low space and power consumption or the temperature programmable oven of a standard gas chromatograph. The heated oven in which the column is immersed must be heated during analysis to a temperature that corresponds to the temperatures of the injector and detector to eliminate cold spots. The capillary GC column (2) is introduced as shown in FIG. 2 into a metal tube (4) that can be resistively heated and that possesses an inlet (5) and an outlet (6), both of which are connected to a current programmed power supply (7) via electrical connections (8). The power supply (7) includes temperature sensor feedback and is capable of being current programmed to provide a temperature program (with time). The temperature can be measured with a thermocouple (9), or via the resistance of the metal tube which increases with its temperature in known manner. Otherwise, the current value can be used alone to represent the temperature via temperature calibration tables. The capillary column in its resistively heated metal tube is mostly located in an air-cooled enclosure (10) which is placed outside the heated oven or above a standard GC oven if a standard GC oven acts as the heated oven (3). The inlet (5) and the outlet (6) of the heated metal tube are located just at the edge of the heated oven (3) housing so that the portion of it that is not resistively heated is located inside the heated oven so that it will be heated to the heated oven temperature. The portion that is resistively heated is located just outside the heated oven to avoid or significantly reduce its double heating by both the heated oven and resistively heated tube, which can lead into an over-heated column section (hot spot) as well as to avoid unheated sections of the GC column (cold spot) between the resistively heated tube and heated oven. The inlet and outlet union of the heated metal tube provide smooth temperature gradient between portions of the capillary column located inside the GC oven and its portion located inside the heated metal tube. Both hot spot and cold spot, permanent or temporary (during temperature program) appearance are unacceptable. Hot spot causes the reduction of the column lifetime, induces local damage to the column separation film and protective VESPEL™ external film, increases column bleed, degrades thermally labile analytes and can lead to column breakage, while cold spot affects chromatographic peak shape and induces peak tailing and delays or precludes the elution of low volatility analytes. Therefore, the proper location of the inlet (5) and outlet (6) unions and their design is aimed at minimizing both hot and cold spots. The capillary column output is flexibly connected (during analysis) to the separately heated detector transfer line (11) (not shown in FIG. 2). According to the present invention, the detector can be any standard GC detector such as a flame ionization detector (FID), flame photometric detector (FPD), nitrogen phosphorus detector (NPD), electron capture detector (ECD) or thermal conductivity detector (TCD) or a mass spectrometer (MS).

Further in accordance with the invention and as shown in FIG. 2 is that the capillary GC column (2) is inserted into the resistively heated metal tube (4) via its inlet (5) and this process of column insertion is aided by the use of an ultrasound source that has an ultrasonic vibrating tip (13) (also known as probe or finger) that touches the heated metal tube (4) during column insertion while this tip is held by the hand-piece (14) and is powered by the ultrasound power supply (15). The inventors found that the touching of the heated metal tube during column insertion (when naturally it is not heated) with a high frequency vibrating device surprisingly dramatically reduces the friction between the column and metal tube and renders the column insertion a very fast, easy and safe process. The simplest to find and use ultrasonic probe is that of dentists that has a power supply that can control the ultrasound power, cable, hand-piece and ultrasonic vibrating scaling tip. Since the ultrasound device is operated only for 2-3 minutes which is easily sufficient for inserting the capillary column, no cooling water is needed. A typical dentist ultrasound device is operated at 28 KHz (in the range of 25-50 KHz).

The installation (insertion) of a new capillary column into the coiled metal heating tube of the fast GC is performed by pushing it inside the metal tube through its inlet union. This insertion process is accompanied by increasing frictional force. The insertion force is increased with the length of the column and can become so strong that the column could be stacked or broken. The same effect takes place during column removal, except that in this case the frictional force acts in the opposite direction. Furthermore, any imperfection of the metal tube inner surface exacerbates the situation. The high frequency vibrations that are imparted on the metal tube-column system induce a detachment (averaged in time and on column length) of the column surface from the metal tube surface, hence almost eliminate or dramatically reduces the friction force to an unexpected degree. As a result, the column slips inside the metal tube on all its length with just a slight pushing/pulling force that is applied to its end that protrudes from the metal tube end. Consequently the installation and/or removal of the column in the fast GC becomes a very easy, fast and safe procedure that also allows the usage of columns with outer diameters just a little smaller than the metal tube inner diameter, as well as multiple columns or multiple column loops installation.

While the essence of the fast GC according to the invention are shown in FIGS. 1 and 2 as described above, additional details as below can further help in improving the description and in illuminating some additional aspects of the fast GC according to the invention.

In the example given above in the description of FIG. 1, a 2 m long heated stainless steel tube with 1.27 mm internal diameter was used. It required a 10 A, 24 V programmable power supply and can accommodate four standard GC column loops with column OD (outer diameter) of 360 µm that can have internal diameters of 100, 150, 180, 200 or 250 µm. Clearly one can use bigger heated metal tubes such as with 3.17 mm OD (⅛") and 2.6 mm ID and in this tube the number of loops can be over 16. However, for fast GC analysis the added column length prevents effective fast analysis with fast temperature program rates thus the use of such long (30 m column) can serve mostly for heart cutting GC-GC or for low energy consumption field GC while for fast GC laboratory use maximum column length of 8 m is usually sufficient. We note that the use of 3.17 mm OD heated tube can require 40 A heating current which is not convenient but can be achieved. Thus, in conclusion, the use of multi column loops allows for the selection of optimal heated tube internal diameter according to target needs. It provides flexible choice of column length and minimizes the power supply dimensions, cost and heating power requirement.

In the example given in FIG. 2 the friction reduction during column insertion into the heated metal tube was achieved with the use of dentist's type of ultrasonic vibrating tip operated at 28 KHz. Clearly other frequencies and vibrating devices can be used and we explored several such devices and frequencies and found that both 20 KHz and 50 KHz are effective while 800 Hz has a noticeable but low effect. Thus, we feel that the range of 500 Hz to 500 KHz could be of potential value. We further note that the use of an ultrasonic device to help with column insertion into the heated metal tube is valuable not only for facilitating the insertion of many loops but also in the insertion of a single loop column when the OD of the single column is close to the ID of the heated metal tube. This way one can minimize the thermal mass and the power consumption of the fast GC.

This invention relates to both the use of heated metal tube with multiple column loops and the use of ultrasonic vibrating device for the reduction of friction during column insertion into the heated metal tube. While these are two separate attributes of the fast GC according to the present invention, they are related and the effectiveness of each one of them depends on the other. The use of heated metal tube with larger internal diameter clearly reduces the friction during column insertion. However, it comes with the penalty of needing a larger power supply and having bigger thermal mass. Thus, a good reason to employ a heated tube having such a large internal diameter is that it enables the use of multiple loops with flexibility in the choice of column length. This important benefit, however, is best realized by using the ultrasonic vibrating device for easier column insertion as the friction during insertion of multiple loops column increases and the chance of the column breaking during the insertion of a long column is much higher. Thus, a preferred method of fast GC according to this invention is to use both a heated metal tube with a larger ID that enables multiple column loops and an ultrasound vibrating device. One feature of the fast GC according to the present invention, is that the capillary column is not rigidly connected to the metal tube and can freely slide (inserted) into it. Therefore, the column can be pushed into the heated metal tube or pulled out and as a result column replacement can be performed by the user at relatively little cost. In order to help the column insertion, in addition to friction reduction via the help of the ultrasonic vibrating device, the fast GC heating metal tube is located in its housing as a relatively large circular structure (i.e., with 12 cm diameter) with smooth curves while entering into the heated oven. In addition, both the inlet and outlet ends (unions) of the metal tube are machined with conical surfaces, typically having an angle of 60° to ease the column insertion with reduced danger of breaking it. Furthermore the column is inserted in such a way that both ends of the capillary column protrude out of the heated metal tube to provide easy connection with both the injector and detector transfer line. Thus, column replacement can be performed with a small portion of a standard capillary column (such as 30 m long) that is cut to a length longer than the length of the heating metal tube, such as about 3 m for a 2 m length heating metal tube. As a result, there is no need to replace or even to disassemble the heating metal tube and its holding structure when the capillary column is replaced. Note that as a result the capillary column is not bundled with its metal tube heater and its mounting holder. Consequently, the user can select and install in the fast GC according to the invention any fused silica GC column from a huge set of commercially available columns (column internal diameters, film types, film thicknesses) from several manufacturers. The combination of choice of a number of single or multiple loops and column extension length before and after the heating metal tube further enables flexible choice in column length, and its periodic trimming if its input end is contaminated by low volatility sample matrix, and provides easy handling when inserting the capillary column into both the GC injector and detector transfer line.

The method of fast GC according to the invention uses a heated oven that can be designed specifically for this fast GC device and become an integral part of the fast GC, or it can be based on a standard GC oven. This heated oven 3 as shown in FIG. 1 serves as a part of the transfer line from the injector and to the detector during the fast GC operation and thus it must be heated to a temperature around that of the detector transfer line such as in the range of 250-350° C. Since such high temperature can lead to column bleed, the analytical column of the fast GC can also be connected to the injector and detector via unions and deactivated fused silica capillary transfer lines.

As noted above, the mounting of the fast GC module can be on a separately heated oven for having an independently operated fast GC unit that is not linked to any sophisticated, bulky, costly, heavy and power hungry standard GC. Consequently, the fast GC according to the present invention can serve as a field portable fast GC or fast GC-MS with small size, weight and energy consumption. While this heated oven can be specifically designed for the fast GC, it can also be the oven of a standard GC. The main differences between a specifically designed oven and the oven of a standard GC is that the specifically designed oven: a) is much smaller than standard GC ovens since it does not need to accommodate 30 m coiled columns and it serves only to transfer flexible small portion of the GC capillary column; b) does not require having a steady internal flow of cooling or heating air with their air input and exit posts; c) does not require medium speed temperature programming capability as that of standard GC ovens; d) does not require precise temperature control and stabilization since it serves only as a heated transfer line and not for the chromatography separation; e) can have the fast GC according to the present invention from all directions while it is preferably mounted on the upper side of standard GC oven since the latter includes holes in the oven in the injectors and/or detectors areas. However, while clearly a specifically designed heated oven is much simpler, smaller, consumes less energy and costs less, the standard GC oven is usually available, and already includes GC injectors, detectors, autosamplers and data analysis software thus can be used 'as is', which is an important advantage.

While most fast GC are based on modules that aim at the conversion of a standard GC into a fast GC, these modules are usually located inside the standard GC oven, while an available design is based on the conversion of the standard GC front oven door into the fast GC module holder. A possible arrangement of the fast GC according to the invention is based on the mounting of the fast GC module on top of the oven of a standard GC. Consequently, the fast GC is typically interfaced with the standard GC through available holes for a second injector or detector. An important advantage in such mounting is that the standard GC oven door can be fully and freely open as usual for service including for column assembly and its connection and insertion into the injector and detector. The fast GC according to the present invention when installed on a standard GC oven does not affect the use of the standard GC if needed. The standard GC column can be kept inside the standard GC oven and can be connected to additional injector and to a detector. This arrangement also implies that the fast GC module is relatively small and that its control electronics can be separated from it and conveniently located at a side of the GC. While the fast GC module is relatively small, it is designed to be big enough to accommodate the resistively heated metal tube in a circular diameter of about 10-15 cm while being mounted on a holder via the support of objects with very low thermal contact with the heated metal tube such as thin Kapton foils or thin glass tubes that are also good thermal insulators to minimize the cooling of the metal tube that might touch it. The fast GC module typically further include an air cooling fan which can be time programmed to facilitate faster cooling down of the metal tube heater when needed.

While the fast GC according to the present invention can be designed as an independent fast GC system it also targets the conversion of a standard GC with its injector and detector into a fast GC. Thus, such a conversion is preferably performed without the removal of any substantial component from the standard GC, including the GC autosampler, injector, detector, pneumatic system and gas flow controls and data analysis and software. As a result, a standard GC can be converted into a fast GC by a simple add-on low cost fast GC device according to the present invention.

Summary of Unique Features of the Fast GC According to the Present Invention

The following are major aspects and advantageous features of the novel fast GC method and device, which differentiate it from known fast GC:

1. Flexible column length. The length of the column according to our method and device is flexible for two reasons: a) the column can extend beyond the heated metal tube of the fast GC module at any desirable length. As a result, the user does not need to have a precise precut column and can have flexibility and ease in column assembly and replacement without a danger of column breakage as well as periodic contaminated column trimming at its injector side. b) as specifically described in the present application and in FIG. 1, the fast GC user can select any number of column loops inside the heated metal tube (from 1 to 4 or more, depending in the heated metal tube ID) and obtain in this way an optimal trade-off of analysis time and GC separation efficiency. This unique capability also minimizes the fast GC energy consumption and its power supply size, weight and cost.

2. Easy and Safe Fast GC Column Replacement. The use of an ultrasound-based vibrating tool for aiding column insertion into the fast GC heated metal tube significantly reduces the friction in the process of column insertion and makes it easy, fast and fully safe. The same applies for column removal. As a result, column replacement can be uniquely performed by untrained fast GC users without demounting of the heated metal tube or any other fast GC part. Furthermore, the use of this vibrating tool uniquely enables and simplifies the insertion of the capillary in multiple loops into a heated metal tube with larger internal diameters and thus helps in bringing the multiple loops advantages of enhanced GC separation with very low thermal mass fast GC.

3. Flexible connections with the GC injector and detector inside a heated oven. GC is much more than just the GC oven and as a system it includes an autosampler, injector and its gas supply system, separation column and its flow rate control, GC oven and its temperature control, detector and means for data analysis and reporting. Thus, it is highly desirable to convert a standard GC into a fast GC via the replacement of only its oven with a fast GC oven module. According to the invention, we use a highly flexible and non-rigid capillary column for the connection of the fast GC heated metal tube with the GC injector and detector. Since our connections are flexible, we must uniquely operate our fast GC with a hot oven being either a dedicated small oven or the oven of a standard GC to prevent cold spots between the fast GC module and the standard GC injector and detector.

4. Having a heated oven base of the fast GC. Our method is different from other low thermal mass (LTM) fast GC in having an additional heated oven for its mounting that is heated in accordance with and in relationship to the injector and detector transfer line temperatures to prevent cold spots at the "naked" flexible sections of the separation capillary column. Thus, our method and device are uniquely characterized in having a heated oven actively participating in the elimination of cold spots between the fast GC and injector and/or detector. Consequently, the heated oven temperature according to the present invention is user defined and not at room temperature.

5. Increased fast GC column lifetime. The analytical column lifetime is significantly extended with fast GC for a number of reasons. Since according to our method short wide bore columns with 0.53 mm internal diameter (ID) can be used they are much more robust than thinner columns with lower ID. Furthermore, since our column freely extends beyond the heating metal tube it can be cut as needed to remove its upstream portion near the injector which is periodically contaminated by low volatility matrix compounds and dirt.

6. Lower cost of columns and use. The price of columns according to the method and device described herein is far lower than with known fast GC methods and devices since our replacement column is just a piece of any standard capillary GC column of choice, (with no preassembled structure) and the column lifetime is much longer due to the ability to trim its contaminated injector side. With our fast GC the user need to replace only the capillary column itself using the same heated metal tube and other fast GC elements, which is in contrast to other fast GC methods. Currently, fast GC short columns are sold for about $2,000 while 30 m standard GC columns are sold for $500. A new column that is used with our fast GC is typically a 3 meter capillary that is cut from a standard 30 m column; hence its cost is only about $50. We note that in other fast GC devices the column is either permanently combined with its heating oven or requires a special coating for microwave heating or resistive heating which restricts its available selection and markedly increases its price. Furthermore, the fact that a new column can cost as little as $50 and it can be available from broad range of capillary column vendors means that the fast GC user can test several column types to properly optimize the column type to his/her specific application need.

7. Flexible fast GC module which is compatible with any standard GC model or can serve as a standalone custom made Fast GC. According to the method and device described herein, the fast GC module is external to a heated oven and only a non-rigid flexible capillary column extends beyond its low thermal mass heating tube. As a result, the heated capillary transfer oven can be any custom designed oven or the oven of a standard GC and the capillary column can be connected in its standard way with any GC connector style of the injector and detector, including with a mass spectrometer detector. Consequently, a single model of the fast GC according to the invention can be coupled with any standard GC system of any vendor using a suitable model specific mount. On the other hand it can be specifically designed for serving as a field portable fast GC or fast GC-MS.

8. Fastest Fast GC module. The fast GC method according to the invention is characterized by very low thermal mass of its heating tube, hence, in combination with short columns and high column flow rates it enables the fastest heating and cooling back rates and thus enables sub one-minute full analysis cycles time for broad range of applications. Our fast GC is unique in having a thin metal tube as its heater without any insulation from ambient air, thereby enabling maximum heat exchange rate and as a result a very fast cooling rate. Furthermore, by using multiple column loops inside the heated metal tube the thermal mass of the fast GC per unit column length is further reduced proportionally to the number of loops.

9. Combined fast GC and standard GC in a single system. Our method and device are further characterized by improved operational flexibility in having the ability to connect two (or three) columns to the same detector via a standard T union. Thus, one can use the fast GC module in combination with a standard GC column that is connected to a second standard GC injector. As a result, our fast GC can uniquely serve for screening, while in the case of detection of a suspected compound, the method can be changed by a click of the mouse and the screening can be followed by a confirmation run with increased separation power of a standard length GC column. The feature of flexible dual use of fast GC and standard GC in a single GC system is of considerable practical importance.

The combination of the advantages above is surprisingly effective and the fast GC according to the present invention provides powerful new methods and devices for obtaining fast GC sample separation for its analysis in combination with standard GC or as a standalone fast GC unit and with all types of GC detectors including the mass spectrometer detector.

What is claimed is:

1. A method for fast gas chromatography analysis, said method comprising:
    injecting a sample to be analyzed into a gas chromatograph injector that is flexibly coupled to a gas chromatography capillary column;
    transferring said sample in said injector into said capillary column with a carrier gas flow;
    transferring said capillary column through a heated oven as a flexible non-rigid capillary into a resistively heated metal tube having opposing input and output ends;
    locating the input and output ends of said resistively heated metal tube near a hole in said heated oven body so that a substantial portion of said column in said heated metal tube is located outside said heated oven and so that said input and output ends project a short distance inside said heated oven;
    introducing an end of said portion of said capillary column that is outside the heated oven from said heated metal tube into said heated oven as a flexible capillary, wherein the capillary column and the resistively heated metal tube are configured such that transferring the capillary column through the heated oven into the resistively heated metal tube and introducing the capillary column from the heated metal tube into the heated oven is reversible, without removal of the resistively heated metal tube;
    connecting said flexible capillary with a transfer line that leads into a gas chromatograph detector;
    connecting both ends of said resistively heated metal tube to a power supply; and
    resistively heating said heated metal tube in a time programmed manner to facilitate fast temperature program of said capillary column;
    wherein:
    the resistively heated metal tube has an internal diameter that is over twice the external diameter of the capillary gas chromatograph column.

2. The method according to claim 1, including inducing high frequency vibrations in said heated metal tube during the insertion therein or removal therefrom of said capillary column.

3. The method according to claim 1, wherein a length of said capillary gas chromatograph column is in a range of 0.2-60 meters.

4. The method according to claim 1, including heating said heated oven to a temperature that corresponds to that of the detector transfer line so that said heated oven serves as a portion of transfer lines of said fast gas chromatograph from the injector and to the detector.

5. The method according to claim 1, wherein said capillary column is cut from a capillary column without its assembly on a mounting tool or bundling with a heater and/or insulation material.

6. The method according to claim 1, wherein said resistively heated metal tube is located and mounted on a heated oven that is designed specifically for the performance of fast gas chromatography analysis.

7. The method according to claim 1, wherein said fast gas chromatograph is an accessory for the conversion of a standard gas chromatograph into a fast gas chromatograph as an add-on device without the removal of any substantial component from the standard gas chromatograph.

8. The method according to claim 1, wherein said resistively heated metal tube is located and mounted on top of a standard gas chromatograph oven.

9. The method according to claim 1, wherein said resistively heated metal tube is located in an enclosure and said enclosure further includes a time-programmable air cooling fan.

10. The method according to claim 1, including introducing more than one capillary gas chromatograph column into the resistively heated metal tube.

11. The method according to claim 1, including introducing more than one loop of capillary gas chromatograph column into the resistively heated metal tube.

12. A method for fast gas chromatography analysis, said method comprising:
injecting a sample to be analyzed into a gas chromatograph injector that is flexibly coupled to a gas chromatography capillary column;
transferring said sample in said injector into said capillary column with a carrier gas flow;
transferring said capillary column through a heated oven as a flexible non-rigid capillary into a resistively heated metal tube having opposing input and output ends;
locating the input and output ends of said resistively heated metal tube near a hole in said heated oven body so that a substantial portion of said column in said heated metal tube is located outside said heated oven and so that said input and output ends project a short distance inside said heated oven;
introducing an end of said portion of said capillary column that is outside the heated oven from said heated metal tube into said heated oven as a flexible capillary, wherein the capillary column and the resistively heated metal tube are configured such that transferring the capillary column through the heated oven into the resistively heated metal tube and introducing the capillary column from the heated metal tube into the heated oven is reversible, without removal of the resistively heated metal tube;
connecting said flexible capillary with a transfer line that leads into a gas chromatograph detector;
connecting both ends of said resistively heated metal tube to a power supply; and
resistively heating said heated metal tube in a time programmed manner to facilitate fast temperature program of said capillary column; and
inducing high frequency vibrations in said heated metal tube during the insertion therein or removal therefrom of said capillary column.

13. The method according to claim 12, wherein the resistively heated metal tube has an internal diameter that is over twice the external diameter of the capillary gas chromatograph column.

14. The method according to claim 12, wherein said high frequency vibrations have a frequency in the range of 500 Hz up to 500 KHz.

15. The method according to claim 12, wherein a length of said capillary gas chromatograph column is in a range of 0.2-60 meters.

16. The method according to claim 12, wherein said capillary column is cut from a capillary column without its assembly on a mounting tool or bundling with a heater and/or insulation material.

17. The method according to claim 12, wherein said resistively heated metal tube is located and mounted on a heated oven that is designed specifically for the performance of fast gas chromatography analysis.

18. The method according to claim 12, wherein said fast gas chromatograph is an accessory for the conversion of a standard gas chromatograph into a fast gas chromatograph as an add-on device without the removal of any substantial component from the standard gas chromatograph.

19. A fast gas chromatograph device for obtaining fast gas chromatography analysis, said device comprising:
a gas chromatograph injector,
a gas chromatograph detector,
a capillary gas chromatography column,
a connector for connecting said capillary column with said gas chromatograph injector,
a source of carrier gas flow for the transferring of sample vapor in said injector into said capillary column,
a metal tube having opposing input and output ends that is adapted to be resistively heated and that is located mostly outside a heated oven and that is coupled via a flexible capillary column to said gas chromatograph injector and detector,
a transfer line with a connector for flexibly connecting said flexible capillary column to a gas chromatograph detector,
said input and output ends of said metal tube being located near a hole in said heated oven body so that a substantial portion of said column in said metal tube is located outside said heated oven,
means for coupling a power supply to both ends of said metal tube for its resistive heating, and
a controller configured for resistively heating said metal tube in a time programmed manner to facilitate fast temperature program of said capillary column in said heated metal tube, wherein the capillary column and the resistively heated metal tube are configured to provide for changing the capillary column without detaching and changing the resistively heated metal tube;
the resistively heated metal tube having an internal diameter that is over twice the external diameter of the capillary gas chromatograph column.

20. The device according to claim 19, further comprising a vibrating device for inducing high frequency vibrations into said heated metal tube during insertion or removal of said capillary column.

21. The device according to claim 19, wherein the heated oven is adapted to serve as a portion of transfer lines of said fast gas chromatograph from the injector and to the detector by heating the heated oven to a temperature that corresponds to that of the detector transfer line.

22. The device according to claim 19, wherein said heated oven is an integrated portion of the fast gas chromatograph that is designed for independent standalone operation.

23. The device according to claim 19, wherein said heated oven is constituted by an oven of a standard gas chromatograph.

24. The device according to claim 19, wherein said metal tube is located and mounted on top of a standard gas chromatograph oven.

25. The device according to claim 19, wherein said capillary column is cut from a standard gas chromatography capillary column without requiring assembly on a mounting tool or bundling with a heater and/or insulation material.

26. The device according to claim 19, further comprising an enclosure with an air cooling fan.

27. The device according to claim 19, further comprising a T-connector for the simultaneous connection of said capillary column with another capillary column for enabling fast switching between standard gas chromatography analysis and fast gas chromatography analysis without a change of hardware.

28. The device according to claim 19, including more than one capillary gas chromatograph column in the resistively heated metal tube.

29. The device according to claim 19, including more than one loop of capillary gas chromatograph column in the resistively heated metal tube.

30. A fast gas chromatograph device for obtaining fast gas chromatography analysis, said device comprising:
a gas chromatograph injector, a gas chromatograph detector,
a capillary gas chromatography column,
a connector for connecting said capillary column with said gas chromatograph injector,
a source of carrier gas flow for the transferring of sample vapor in said injector into said capillary column,
a metal tube having opposing input and output ends that is adapted to be resistively heated and that is located mostly outside a heated oven and that is coupled via a flexible capillary column to said gas chromatograph injector and detector,
a transfer line with a connector for flexibly connecting said flexible capillary column to a gas chromatograph detector,
said input and output ends of said metal tube being located near a hole in said heated oven body so that a substantial portion of said column in said metal tube is located outside said heated oven,
means for coupling a power supply to both ends of said metal tube for its resistive heating, and
a controller configured for resistively heating said metal tube in a time programmed manner to facilitate fast temperature program of said capillary column in said heated metal tube, wherein the capillary column and the resistively heated metal tube are configured to provide for changing the capillary column without detaching and changing the resistively heated metal tube, and
a vibrating device for inducing high frequency vibrations into said heated metal tube during insertion or removal of said capillary column.

31. The device according to claim 30, wherein the resistively heated metal tube has an internal diameter that is over twice the external diameter of the capillary gas chromatograph column.

32. The device according to claim 30, wherein said heated oven is an integrated portion of the fast gas chromatograph that is designed for independent standalone operation.

33. The device according to claim 30, wherein said heated oven is part of a standard gas chromatograph.

34. The device according to claim 30, wherein said capillary column is cut from a standard gas chromatography capillary column without requiring assembly on a mounting tool or bundling with a heater and/or insulation material.

* * * * *